Figure 1:
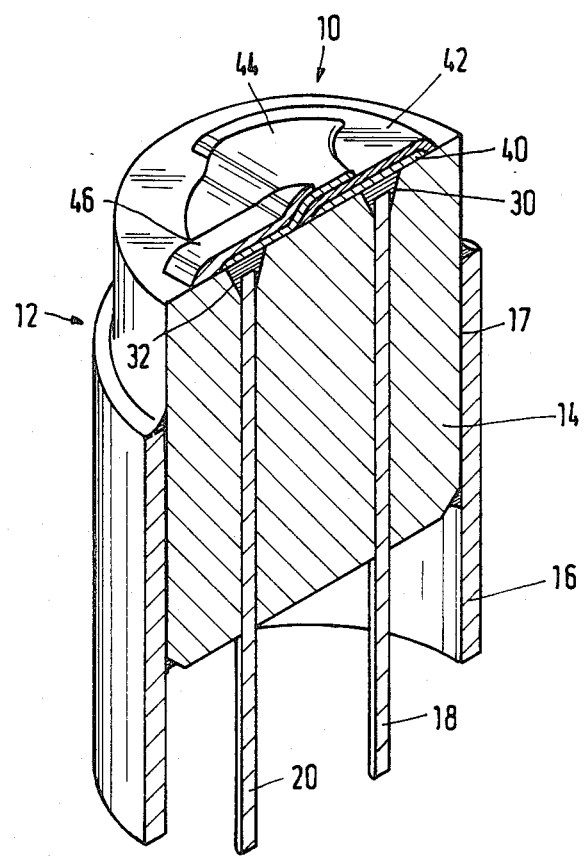

United States Patent [19]

Woest et al.

[11] Patent Number: 4,530,030
[45] Date of Patent: Jul. 16, 1985

[54] THIN-FILM HUMIDITY SENSOR FOR MEASURING THE ABSOLUTE HUMIDITY AND METHOD FOR THE PRODUCTION THEREOF

[75] Inventors: Wolfgang Woest, Rheinfelden; Rainer Silbermann; Frank Hegner, both of Schopfheim, all of Fed. Rep. of Germany

[73] Assignee: Endress u. Hauser GmbH u. Co., Fed. Rep. of Germany

[21] Appl. No.: 564,212

[22] Filed: Dec. 22, 1983

[30] Foreign Application Priority Data

Apr. 12, 1983 [DE] Fed. Rep. of Germany ....... 3313150

[51] Int. Cl.³ .............................................. H01G 5/20
[52] U.S. Cl. ..................................... 361/286; 73/336.5
[58] Field of Search ........................ 361/286; 73/336.5

[56] References Cited

U.S. PATENT DOCUMENTS 2,975,638 3/1961 Morrison .......................... 73/336.5

Primary Examiner—Donald A. Griffin
Attorney, Agent, or Firm—Murray, Whisenhunt and Ferguson

[57] ABSTRACT

A thin-film humidity sensor for measuring the absolute humidity having a base electrode, a moisture-sensitive dielectric layer and a top electrode is formed at the end face of an electrically insulating bushing body by the thin-film technique. The connecting conductors are led through the bushing body and terminate in contact areas which are ground plane and polished together with the end face of the bushing body. The metal layers forming the electrodes are so shaped on application, preferably by means of perforated masks, that they each cover the contact area of the associated connecting conductor and are electrically connected thereto. The bushing body is inserted into a sleeve of a highly alloyed nickel-molybdenum compound and connected thereto in pressure-resistant manner.

13 Claims, 3 Drawing Figures

THIN-FILM HUMIDITY SENSOR FOR MEASURING THE ABSOLUTE HUMIDITY AND METHOD FOR THE PRODUCTION THEREOF

The invention relates to a thin-film humidity sensor for measuring the absolute humidity comprising a bushing body at the end face of which are disposed a metallic base electrode, a moisture-sensitive dielectric layer and a metallic top electrode, and having at least one lead-through conductor which is led through the bushing body and electrically connected to one of the two electrodes.

In a known humidity sensor the bushing body is an aluminum tube which is sealed at the end face and which forms both the base electrode of the humidity sensor and the electrical connection of the base electrode. On the end face, by anodic oxidation of the aluminum a layer of porous aluminum oxide is formed which represents the moisture-sensitive dielectric. A gold layer which is so thin that it is water-permeable is vapor deposited onto the aluminum oxide layer. The connecting conductor to said gold layer runs through the interior of the aluminum tube and is led in an electrically insulated manner through the end wall thereof and through the aluminum oxide layer up to the gold layer.

This known humidity sensor has a very robust and pressure-resistant construction. It is however relatively expensive because its production requires precision machining. In addition, there is the great disadvantage that the humidity sensor consists substantially of aluminum and that as regards the material and ensuring resistance to flame break-through along its periphery in the installed condition is not very suitable for use in areas where there is a danger of explosion. The entire bushing body consists of metal and forms one of the connecting conductors. For this reason, the humidity sensor has a considerable capacitance with respect to ground so that it is susceptible to external electromagnetic alternating fields. An object of this invention is the provision of a thin-film humidity sensor for measuring the absolute humidity which ensures along its periphery the break-through resistance required for use in areas where there is a danger of explosion.

Another object of this invention is to provide a thin-film humidity sensor which largely dispenses with the use of aluminum and consequently is suitable without restriction for use in areas where there is a danger of explosion.

Another object of this invention is to provide a thin-film humidity sensor which with simple production has a very robust and pressure-resistant construction, the capacitance of which with respect to ground is small.

Another object of this invention is to provide a thin-film humidity sensor in which all the connecting conductors are led outwardly independently of the bushing body carrying the humidity sensor and are not in contact with the medium to be measured.

According to the invention these objects are achieved in that the bushing body consists of electrically insulating material, that at least two lead-through conductors are led spaced apart through the bushing body in such a manner that their end-face contact areas are flush with the end face of the bushing body, that the base electrode is disposed on a portion of the end face of the bushing body in such a manner that said electrode covers the contact area of one lead-through conductor and is electrically connected thereto, that the moisture-sensitive dielectric layer is disposed on the base electrode, and that the top electrode is applied to at least a portion of the moisture sensitive layer and to at least a portion of the end-face of the bushing body not covered by the base electrode in such a manner that said top electrode covers the contact area of a further lead-through conductor and is electrically connected thereto.

A particular advantage of the humidity sensor according to the invention resides in that the moisture-sensitive system including the base electrode can be formed by the known thin-film technique at the end face of the bushing body, the contacting of the two electrodes taking place automatically on application of the thin metal layers. The production is therefore very simple and requires no precision machining. A further advantage is that no organic substances such as adhesives, lacquers, etc. are used, whereby moisture accumulators are avoided and the humidity sensor is largely resistant to organic solvents so that the functional reliability is considerably improved.

It has surprisingly been found that the thin-film humidity sensor according to the invention even with relatively large thickness of the moisture-sensitive layer, which may be 0.0006 mm and more, operates independently of the temperature and consequently can be used for measuring the absolute humidity.

A preferred embodiment of the thin-film humidity sensor according to the invention resides in that the bushing body is inserted into a sleeve of a highly alloyed nickel-molybdenum compound, for example Hastelloy C, and joined thereto in pressure-resistant manner. This embodiment fulfills in particularly satisfactory manner the requirements which are made for use in areas where there is a danger of explosion.

Advantageous further modifications and embodiments of the humidity sensor according to the invention and a preferred method of the production thereof are characterized in the subsidiary claims.

Figure 2:
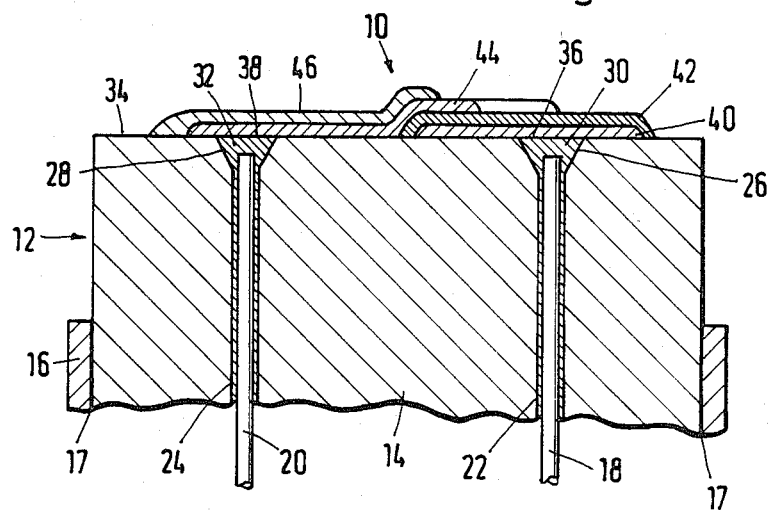
Figure 3:
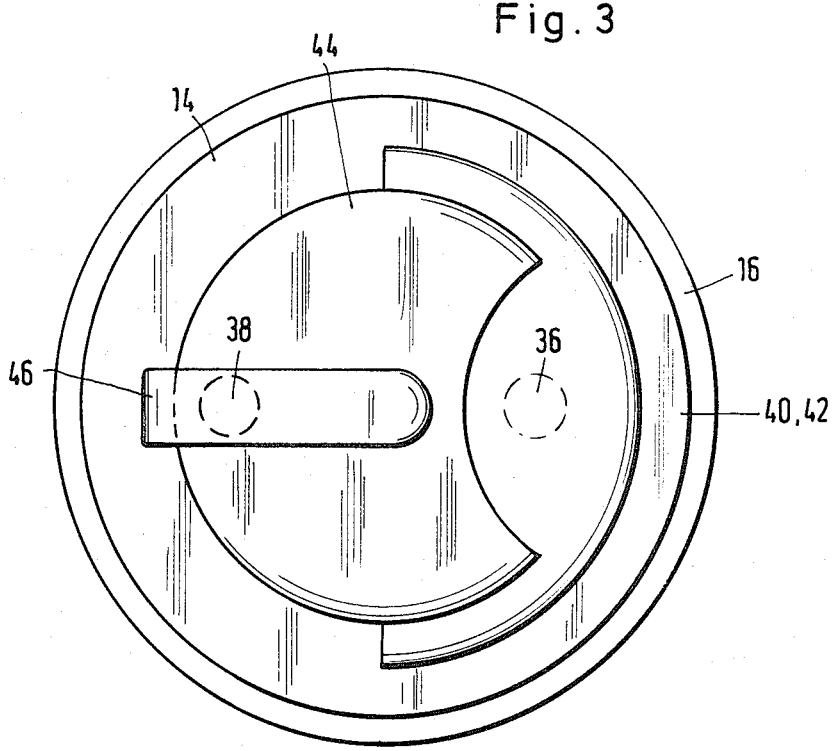

Further advantages and features of the invention will be apparent from the following description of an example of embodiment with the aid of the drawings, wherein:

FIG. 1 shows a perspective sectional view of a humidity sensor according to the invention, FIG. 2 is a cross-section through the upper part of the bushing body and the metal layers applied thereto FIG. 3 is a plan view of the humidity sensor of FIG. 2.

The humidity sensor 10 illustrated in the drawings is formed by the thin-film technique at the end face of a pressure-resistant bushing 12.

The bushing 12 comprises a cylindrical bushing body 14 of insulating material which is inserted into a sleeve 16 of a suitable material and connected to said sleeve in pressure-resistant manner, for example by a brazed connection 17. The bushing body 14 may be a ceramic molding, for example of aluminum oxide.

The sleeve 16 consists preferably of a highly alloyed nickel-molybdenum compound, for example Hastelloy C, and it may be nickel-plated. Silver-copper-eutectic may be used for the joint 17 between the bushing body 14 and the sleeve 16.

The electrical connection of the humidity sensor 10 is via lead-through conductors 18, 20 which are led through the bushing body 14 in pressure-resistant manner. The lead-through conductors 18, 20 are for example pins of covar.

The construction of the humidity sensor 10 is best understood from the following description of a preferred method of production.

The ceramic molding forming the bushing body 14 comprises two axial bores 22, 24 (FIG. 2) which at the face end merge into a conical widening 26 and 28 respectively. The lead-through conductors (covar pins) 18, 20 are introduced into the bores 22, 24 in such a manner that they project into the conical widenings 26 and 28 and are connected in pressure-resistant manner to the bushing body 14 by means of brazing solder 30, 32 which also fills the conical widenings 26, 28. Once again, silver-copper eutectic may be used as brazing solder. After soldering-in the lead-through conductors 18, 20 the end face 34 of the bushing body 14 together with the endface brazed areas are ground plane and polished. The brazing solder 30, 32 disposed in the conical widenings 26 and 28 then forms at the end face contact areas 36, 38 which lie in a plane with the end face 34 of the bushing body 14.

As next step, a thin aluminum layer 40 is applied to a part of the end face 34 of the bushing body 14 in such a manner that said layer 40 covers the contact area 36 but leaves the contact area 38 free. In the example of embodiment illustrated the aluminum layer 40 is semicircular. The aluminum layer 40 is applied by one of the known methods of the thin-film technique, for example by cathode sputtering or vapor deposition. The aluminum layer has a thickness of more than 1 $\mu$m and is applied in such a manner that an electrically well conducting connection is obtained between the aluminum layer 40 and the contact area 36. In this manner, the aluminum layer 40 is electrically connected to the lead-through conductor 18.

It is advantageous to dispose between the contact area 36 and the aluminum layer 40 a diffusion barrier layer of titanium nitride or other suitable material. This barrier layer prevents the diffusion of copper and silver atoms from the brazing solder 30 into the aluminum of the aluminum layer 40. Such a contamination could have troublesome effects in the subsequent anodizing process. The application of the barrier layer (which is not illustrated in the drawings) can also take place according to one of the known methods of the thin-film technique, of course in an operation step preceding the application of the aluminum layer 40.

The shaping of the aluminum layer 40 and the barrier layer, if present, can be done with the aid of a perforated mask. This gives a considerable saving of time and costs compared with the shaping by photolithographic methods otherwise usual in the thin-film technique.

After the formation of the aluminum layer 40, by anodic oxidation a layer 42 of 0.0006 mm thickness of porous aluminum oxide is produced on the surface thereof, said aluminum oxide enclosing the aluminum layer 40 all round. For this purpose it is in particular essential that the end face 34 and the contact area 36 are planar and flat and have an extremely small roughness.

The next step is the application of a thin water-vapor permeable metal layer 44 in such a manner that said layer partially overlaps the aluminum layer 40 and the aluminum oxide layer 42 formed thereon and otherwise lies on the end face 34 of the bushing body 14 in such a manner that it covers the contact area 38 left free. The metal layer 44 may consist of gold, nickel, chromium or a similar metal or alternatively of a plurality of superimposed layers of different metals. It is also applied by one of the usual methods of the thin-film technique, preferably using a perforated mask, and once again it must be ensured that an electrically well conducting connection is obtained between the metal layer 44 and the contact area 38.

Finally, to the portion of the metal layer 44 lying above the contact area 38 a contact-reinforcing layer 46 is applied which consists preferably of gold and ensures a good electrical contact between the metal layer 44 and the contact area 38.

The aluminum layer 40 forms the base electrode and the metal layer 44 the top electrode of a capacitor whose dielectric is formed by the porous aluminum oxide layer 42.

The porous aluminum oxide is the actual moisture-sensitive element of the absolute humidity sensor because it adsorbs water vapor from the surroundings or gives off water vapor to the surroundings. The impedance of the capacitor depends on the water vapor content of the aluminum oxide layer 42 and is therefore a measure of the water vapor content of the surrounding gas.

The sleeve 16 is introduced in pressure-tight manner into the opening of a screw-in member, not illustrated, and welded to said member. When using the absolute humidity sensor the screw-in member is then screwed by means of its thread into the wall of a container, tube or other space in which the medium whose humidity is to be measured is disposed. The electrical terminals of the capacitor forming the humidity sensor are then led outwardly through the bushing body 14 with which they are connected in pressure-resistant manner so that they do not come into contact with the measured medium. Only the parts of the humidity sensor formed by the thin-film technique at the end face 34 of the bushing body are exposed to the measured medium. This largely eliminates all causes of measuring errors. In the measuring space there are no corners and gaps and no organic material, such as adhesive joints, which can act as moisture accumulator and falsify the measurement. The capacitance of the humidity sensor with respect to ground and thus the susceptibility to external electromagnetic alternating fields is small. Since the connecting conductors do not come into contact with the measured medium there is no danger of parallel resistances which could influence the high-resistance measurement. The construction of the humidity sensor is extremely stable and resistant to pressure so that it is suitable in particular for use under extreme pressure conditions or in areas where there is a danger of explosion. The production can take place without precision machining using conventional thin-film techniques and can be largely automated. The humidity sensor according to the invention can of course also be used for the measurement of the relative humidity by incorporating a temperature measurement.

We claim:

1. Thin-film humidity sensor for measuring the absolute humidity comprising a bushing body at the end face of which a metallic base electrode, a moisture-sensitive dielectric layer and a metallic top electrode are disposed, and comprising at least one lead-through conductor which is led through the bushing body and electrically connected to one of the two electrodes, characterized in that the bushing body (14) consists of electrically insulating material, that at least two lead-through conductors (18, 20) are led spaced apart through the bushing body (14) in such a manner that their end-face contact areas (36, 38) are flush with the end face (34) of the bushing body (14), that the base electrode (40) is disposed on a portion of the end face (34) of the bushing body (14) in such a manner that said base electrode covers the contact area (36) of one lead-through conductor (18) and is electrically connected thereto, that the moisture-sensitive dielectric layer (42) is applied to the base electrode (40) and that the top electrode (44) is applied to at least a portion of the moisture-sensitive layer (42) and to at least a portion of the end face (34) of the bushing body (14) not covered by the base electrode (40) in such a manner that said top electrode covers the contact area (38) of a further lead-through conductor (20) and is electrically connected thereto.

2. Humidity sensor according to claim 1, characterized in that the lead-through conductors (18, 20) are brazed to the bushing body (14), and that the end face (34) of the bushing body with the brazed joints (30, 32) is ground plane and polished.

3. Humidity sensor according to claim 2, characterized in that in the bushing body (14) for receiving each lead-through conductor (18, 20) a bore (22, 24) is formed which widens towards the end face (34) of the bushing body (14), and that the widenings (26, 28) of the bores (22, 24) are filled with the brazing solder (30, 32).

4. Humidity sensor according to any one of claims 1 to 3, characterized in that the bushing body (14) is a ceramic molding.

5. Humidity sensor according to claim 4, characterized in that the ceramic molding (14) consists of aluminum oxide.

6. Humidity sensor according to any one of claims 1, characterized in that the bushing body (14) is inserted into the opening of a sleeve (16) and connected to the latter in pressure-resistant manner.

7. Humidity sensor according to claim 6, characterized in that the sleeve (16) consists of a highly alloyed nickel-molybdenum compound.

8. Humidity sensor according to claim 1, characterized in that the base electrode (40) and the top electrode (44) are formed by metal layers applied by the thin-film technique.

9. Humidity sensor according to claim 1, characterized in that the base electrode (40) consists of aluminum and that the moisture-sensitive dielectric layer (42) is a porous aluminum oxide layer formed as thin film by anodic surface oxidation of the aluminum.

10. Humidity sensor according to claim 1, characterized in that the moisture-sensitive dielectric layer (42) has a layer thickness of about 0.0006 mm.

11. Humidity sensor according to claim 9, characterized in that a diffusion barrier layer is arranged between the base electrode (40) and the underlying contact area (36).

12. Humidity sensor according to claim 11, characterized in that the diffusion barrier layer consists of titanium nitride.

13. Humidity sensor according to claim 1, characterized in that on the portion of the top electrode (44) laying over the contact area (38) of the further lead-through conductor (20) a metal layer (46) is disposed for contact reinforcement.

* * * * *